United States Patent [19]

Wagner et al.

[11] 4,029,812

[45] June 14, 1977

[54] NOVEL HYPOLIPIDEMIC 2-(3,5-DI-TERT-BUTYL-4-HYDROXY-PHENYL)THIO CARBOXAMIDES

[75] Inventors: Eugene R. Wagner, Midland; Larry G. Mueller, Ypsilanti, both of Mich.

[73] Assignee: The Dow Chemical Company, Midland, Mich.

[22] Filed: Feb. 18, 1976

[21] Appl. No.: 658,971

[52] U.S. Cl. .............. 424/298; 260/453 RW; 260/500.5 H; 260/559 T; 424/320; 424/324

[51] Int. Cl.$^2$ .............. A61K 31/21; A61K 31/165; C07C 119/20

[58] Field of Search .......... 260/453 RW, 298, 320; 424/324

[56] References Cited

UNITED STATES PATENTS

| | | | |
|---|---|---|---|
| 2,681,363 | 6/1954 | Schwenk et al. | 424/317 X |
| 3,369,025 | 2/1968 | Bolhofer | 424/263 X |
| 3,383,411 | 5/1968 | Schultz et al. | 260/521 R |
| 3,652,646 | 3/1972 | Leigh et al. | 424/308 X |
| 3,707,549 | 12/1972 | Mills | 424/308 X |
| 3,716,644 | 2/1973 | Alberts et al. | 424/308 |
| 3,732,295 | 5/1973 | Dompé | 424/318 X |

FOREIGN PATENTS OR APPLICATIONS

| | | |
|---|---|---|
| 815,703 | 5/1974 | Belgium |
| 9,072,229 | 11/1972 | Japan |
| 7,333,743 | 10/1970 | Japan |
| 7,333,742 | 10/1970 | Japan |

OTHER PUBLICATIONS

Metz et al., vol. 82, (1975), 43,070h.
Holland, vol. 82, (1975), 16,563q.
Kuroda et al., vol. 80, (1974), 133,072y.
Kuroda et al., vol. 80, (1974), 133,073z.

*Primary Examiner*—Allen J. Robinson
*Attorney, Agent, or Firm*—James W. Ambrosius

[57] ABSTRACT

Novel 2-((3,5-di-tert-butyl-4-hydroxyphenyl)-thio)carboxamides and compositions containing the compounds are disclosed. A method for reducing blood serum lipids using the compounds and compositions of the invention is also disclosed.

7 Claims, No Drawings

NOVEL HYPOLIPIDEMIC 2-(3,5-DI-TERT-BUTYL-4-HYDROXY-PHENYL)THIO CARBOXAMIDES

BACKGROUND OF THE INVENTION

As established by various studies, it is recognized that cholesterol and triglycerides play a major role in the formulation of artherosclerotic plaques by accelerating the deposition of blood lipids in the arterial wall.

Various compounds related to benzoic acid have been described as having hypolipidemic activity or as being useful in the treatment of heart disease. See U.S. Pat. Nos. 3,716,644; 3,732,295; 3,707,549; 3,369,025; and 3,652,646. Foreign references to hypolipidemic compounds or those useful for the treatment of heart disease may be found in CA82:43070h (German Offen. 2,316,914); Belgian 815,703; Japanese 7,333,742 and 7,333,743; CA82:16563q; CA80:133072y and CA80:133073z.

Reference to (3,5-di-tert-butyl-4-hydroxyphenylthio) acetic esters used as antioxidants may be found in the unexamined Japanese application 9,072,229. Other references of interest may be found in U.S. Pat. Nos. 2,681,363 and 3,383,411.

SUMMARY OF THE INVENTION

The present invention relates to novel 2-((3,5-di-tert-butyl-4-hydroxyphenyl)thio)carboxamides and compositions containing these compounds. This invention also relates to methods for reducing plasma lipid levels, especially cholesterol and triglyceride levels, using the compounds of the present invention.

The compounds that are the subject of the present invention may be represented by the general formula

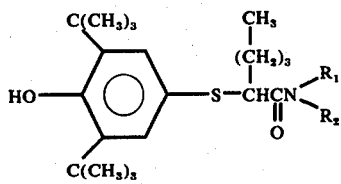

wherein $R_1$ and $R_2$ independently represent hydrogen, a lower alkyl, a lower alkoxy, hydroxy, or a lower hydroxyalkyl.

As used herein the terms lower alkyl, lower alkoxy, and lower alkyl hydroxy refer to radicals having from 1 to 5 carbon atoms.

Compounds of the present invention have shown hypolipidemic activity in animals and in particular in mammals. Hypolipidemic activity refers to the effect of lowering the blood lipid content and in particular the cholesterol and triglyceride content of the serum. The compounds of the present invention are therefore suitable for use in treating serum hyperlipidemia in mammals and in particular are useful for treatment of hypercholesterolemia and hypertriglyceridemia, that is, abnormally high levels of lipids, cholesterol, or triglycerides, respectively, in the serum. The compounds can be administered orally or parenterally by subcutaneous, intravenous, or intraperitoneal injection or by implantation or the like, oral administration being preferred.

The hypolipidemic amount of the carboxamide compounds to be administered to an animal, that is, the amount which is effective to significantly lower the serum lipid level, can vary depending upon such factors as the animal treated, the particular carboxamide employed, the desired lipid level to be obtained, whether or not the animal is hypolipidemic, the period of administration and the method of administration. In general, an effective daily dosage range is from about 1 to 400 mg/kg body weight with a daily dosage range of from about 5 mg/kg to 30 mg/kg of body weight being preferred.

For oral administration, pharmaceutical preparations of the compounds of the present invention may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or codliver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan tri-oleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinyl-pyrrolidone. The emulsions and suspensions may contain conventional excipients such as sweetening agents, flowing agents, coloring materials and preservatives.

The compounds can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anaesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

DETAILED DESCRIPTION OF THE INVENTION

The compounds of the present invention are prepared by treating 2-((3,5-di-tert-butyl-4-hydroxyphenyl)thio)hexanoic acid chloride with a pre-selected amine in an inert solvent such as benzene. The phenylthiohexanoic acid used as a starting material may be prepared by reacting 2,6-di-tert-butyl-4-mercaptophenol with 2-halohexanoic acid. The acid chloride is obtained by treating the above acid with thionyl chloride.

The invention will be more fully understood from the examples which follow.

EXAMPLE 1

Preparation of 2-((3,5-Bis(1,1-dimethylethyl)-4-hydroxyphenyl)thio)-N-ethoxyhexamide A base solution (22 grams of NaOH in 41 milliliters (ml) of water) was added to a solution of 2,6-di-t-butyl-4-mercaptophenol (64.3 grams; 0.27 mole) in 540 ml. of absolute ethanol with stirring while cooling the reaction mixture under nitrogen. Following the base addition, a solution of 2-bromohexanoic acid (52.8 grams; 0.27 mole) in 27 ml. of ethanol was added and the resulting reaction mixture was stirred at room temperature for about 6 hours and left standing overnight. The reaction mixture was then diluted with about 400 ml. of water and acidified with cold 6N HCl. The yellow brown precipitate resulting from the acidification was obtained by filtration, washed with water and recrystallized from a methylene chloride-hexane mixture. As a result of these operations, the desired 2-((3,5-di-tert-butyl-4-hydroxyphenyl)thio)hexanoic acid compound was obtained as a white crystalline solid having a melting point of 140°–142° C. Analysis calculated for $C_{20}H_{32}O_3S$: C, 68.15; H, 9.14; S, 9.10. Found: C, 68.14; H, 9.34; S, 8.86.

The phenylthiohexanoic acid prepared above (20 grams) was refluxed with 25cc of thionyl chloride ($SOCl_2$) until the solid dissolved. The excess thionyl chloride was removed under reduced pressure to leave the acid chloride as a yellow oil.

The acid chloride (3.68 grams, 0.01 mole) prepared above was added in 10 ml. of ether to a mixture of 0.98 grams (0.01 mole) of ethoxyamine hydrochloride, 1.06 grams (0.01 mole) of anhydrous sodium carbonate, and 50 ml. of ether cooled to 0° C. The resulting solution was stirred, and 3.5 ml. of water was added. The reaction mass was stirred at room temperature for 16 hours. The ether layer was washed three times with 40 ml. of water. The organic layer was then dried over magnesium sulfate, filtered and evaporated. A yellow gum (3.86 grams) was left behind. After 7 days in the refrigerator the gum crystallized. The crude crystals of 2-((3,5-Bis(1,1-dimethylethyl)4-hydroxyphenyl)thio)-N-ethoxyhexamide were recrystallized from 50 ml. of hexane. The white crystals were found to have a melting point of 82°–84° C.

The infrared and NMR spectra confirmed the proposed structure. Theoretical analysis of the compound was carbon 66.8%, hydrogen 9.43%, and nitrogen 3.54%. Elemental analysis showed carbon 66.9%, hydrogen 9.45%, and nitrogen 3.87%.

Following the general procedure set forth in the preceding example several other phenylthiocarboxamides were prepared having the general formula:

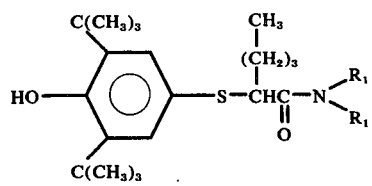

Table I summarizes the results of these studies.

TABLE I

| Example Number | $R_1$ | $R_2$ | Elemental Analysis Theoretical | | | Actual | | | M.P °C | Reaction Solvent |
|---|---|---|---|---|---|---|---|---|---|---|
| | | | C | H | N | C | H | N | | |
| 2 | $CH_2CH_2OH$ | H | — | — | — | — | — | — | Brown Oil* | Ether |
| 3 | $CH_3$ | $CH_3$ | 69.61 | 9.82 | 3.69 | 69.9 | 9.80 | 3.85 | 117–118.5 | Benzene |
| 4 | H | OH | 65.4 | 9.05 | — | 65.5 | 8.82 | — | 148–149.5 | Ether + $Na_2CO_3$ |

*Material was chromatographed on silica gel 60 and eluted with benzene/methanol.

The hypolipidemic effect of the compounds of the invention is illustratively demonstrated in rats. In this procedure, a compound of the present invention is dissolved in acetone, taken up on a silica gel and mixed with normal ground feed to yield concentrations of 0.125 percent of the compound in the animal feed. The treated feed was administered to male rats weighing 150–160 grams over a 14 day period. Following the fourteen day feeding period, the rats were sacrificed, and blood samples were collected. The relative levels of serum cholesterol in the blood samples was determined by the Henly method. A. A. Henly, *Analyst*, 82, 286 (1957). The relative levels of triglycerides in the blood samples were determined by the Van Handel and Zilversmit method. *J. Lab. Clin. Med.* 50, 152 (1957) and *Clin. Chem.* 7, 249 (1961). Taking the average levels of control rats as standard the mean results obtained in the treated groups is thereby ascertained.

The data presented in Table II summarizes the results of the above studies.

TABLE II

| Compound Example No. | Serum Cholesterol | Serum Triglycerides |
|---|---|---|
| 1 | −29%* | −66%* |
| 2 | −10% | −29% |
| 3 | −11% | −14% |
| 4 | −20% | −59% |

*All data represents relative change in values for the treated animals when compared to the control group.

The data indicate that the compounds of Example 1, 2-((3,5-Bis(1,1-dimethylethyl)-4-hydroxyphenyl)thio)-N-ethoxyhexamide, and Example 4, 2-((3,5-Bis(1,1-dimethylethyl)-4-hydroxyphenyl)thio)-N-hydroxyhexamide, were highly active in reducing the levels of serum cholesterol and serum triglycerides in rats when administered according to the procedures described above. The compound of Example 1 reduced the serum triglycerides 66% and the serum cholesterol 29% as compared to the group of control rats. The compound of Example 4 showed decreases of 59% and 20% respectively for triglycerides and cholesterol. The results obtained for the other compounds while somewhat less dramatic also indicated a significant reduction of serum cholesterol and serum triglycerides in test animals as compared to the controls.

I claim:
1. A compound of the formula

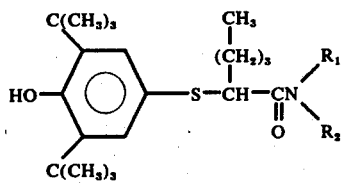

wherein $R_1$ represents lower alkoxy and $R_2$ represents hydrogen, lower alkyl, lower alkoxy, hydroxy or lower hydroxyalkyl.

2. The compound of claim 1 which is 2-((3,5-Bis(1,1-dimethylethyl)-4-hydroxyphenyl)thio)-N-ethoxyhexamide.

3. A method for lowering elevated serum lipids in a mammal which comprises administering internally to the mammal a hypolipidemically effective amount of a compound of the formula:

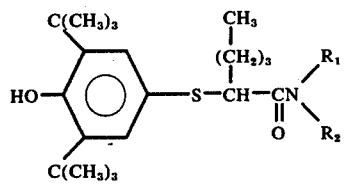

wherein $R_1$ represents lower alkoxy and $R_2$ represents hydrogen, lower alkyl, lower alkoxy, hydroxy or lower hydroxyalkyl.

4. The method of claim 3 wherein the compound is 2-((3,5-Bis(1,1-dimethylethyl)-4-hydroxyphenyl)thio)-N-ethoxyhexamide.

5. The method of claim 3 wherein the mammal is administered 5 mg/kg to 30 mg/kg body weight of the compound.

6. A hypolipidemic composition comprising a suitable pharmaceutical carrier and a hypolipidemically effective amount of a compound having the formula:

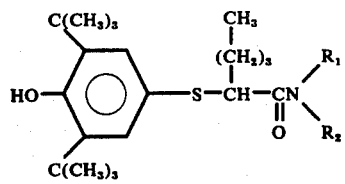

wherein $R_1$ represents lower alkoxy and $R_2$ represents hydrogen, lower alkyl, lower alkoxy, hydroxy or lower hydroxyalkyl.

7. The composition of claim 6 wherein the compound is 2-((3,5-Bis(1,1-dimethylethyl)-4-hydroxyphenyl)thio)-N-ethoxyhexamide.

* * * * *